(12) United States Patent
Mais et al.

(10) Patent No.: US 6,380,441 B1
(45) Date of Patent: Apr. 30, 2002

(54) PROCESS FOR PREPARING 3-HYDROXYBENZYL ALCOHOL

(75) Inventors: Franz-Josef Mais, Düsseldorf; Herbert Diehl, Leverkusen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/949,214

(22) Filed: Sep. 7, 2001

(30) Foreign Application Priority Data

Sep. 12, 2000 (DE) .......................................... 100 44 910

(51) Int. Cl.$^7$ .............................................. C07C 39/10
(52) U.S. Cl. ...................................................... 568/764
(58) Field of Search ......................................... 568/764

(56) References Cited

U.S. PATENT DOCUMENTS

| 3,420,868 A | * | 1/1969 | Weil |
| 3,732,315 A | * | 5/1973 | Hoffmann |
| 4,069,340 A | * | 1/1978 | Pattison |

* cited by examiner

Primary Examiner—Michael L. Shippen
(74) Attorney, Agent, or Firm—Joseph C. Gil; Richard E. L. Henderson

(57) ABSTRACT

3-Hydroxybenzyl alcohol can be prepared in a simple and inexpensive way by subjecting 3-chloromethylphenyl chloroformate to an acidolysis with a carboxylic acid or a carboxylic acid salt and subsequently subjecting the reaction product of the first step to an alcoholysis.

10 Claims, No Drawings

PROCESS FOR PREPARING 3-HYDROXYBENZYL ALCOHOL

BACKGROUND OF THE INVENTION

The present invention relates to a process for preparing 3-hydroxybenzyl alcohol from 3-chloromethylphenyl chloroformate. 3-Hydroxybenzyl alcohol is a valuable intermediate for the preparation of pharmaceutical active compounds.

Various methods of preparing 3-hydroxybenzyl alcohol are known. These methods start from 3-hydroxybenzaldehyde, 3-hydroxybenzoic acid, or derivatives of these compounds. To convert them into 3-hydroxybenzyl alcohol, the starting compounds are reduced.

For example, 3-hydroxybenzoic acid can be reduced using lithium aluminum hydride, using organic aluminum or boron compounds, or by means of electrolysis to give 3-hydroxybenzyl alcohol. A similar reaction is the reduction of 3-hydroxybenzoic esters to 3-hydroxybenzyl alcohol, which can be carried out using aluminum hydrides or boron hydrides.

For the reduction of 3-hydroxybenzaldehyde to 3-hydroxybenzyl alcohol, it is possible to use the following reagents: lithium aluminum hydride, sodium borohydride, zinc borohydride, tin dichloride plus magnesium, sodium amalgam, or polymer-bound nicotinamide-adenine dinucleotide in the H form (NADH). This reaction can also be carried out as a catalytic hydrogenation, e.g., using Raney nickel catalysts or platinum catalysts. The catalytic reduction of benzyl ethers of 3-hydroxybenzyl alcohol is similar.

Further methods of forming 3-hydroxybenzyl alcohol are cleavage of (3-hydroxyphenyl)methyl formate and (3-hydroxyphenyl)methyl 2-nitrobenzenesulfenate. A disadvantage of all of these processes is that relatively expensive materials such as 3-hydroxybenzoic acid, 3-hydroxybenzaldehyde, or derivatives thereof have to be used as starting material. In addition, it is frequently necessary to employ reducing agents or catalytic hydrogenations, which are complicated or expensive.

There is therefore still a need for a process for preparing 3-hydroxybenzyl alcohol simply and inexpensively.

SUMMARY OF THE INVENTION

We have now found a process for preparing 3-hydroxybenzyl alcohol comprising
(a) subjecting 3-chloromethylphenyl chloroformate to an acidolysis with a carboxylic acid or a carboxylic acid salt, and
(b) carrying out an alcoholysis of the reaction product of the acidolysis step.

DETAILED DESCRIPTION OF THE INVENTION

The 3-chloromethylphenyl chloroformate to be used according to the invention is known from the literature. It can be obtained, for example, by phosgenation of m-cresol and subsequent side-chain chlorination of the resulting 3-methylphenyl chloroformate. As catalysts for the phosgenation, it is possible to use, for example, dimethylformamide and phosphorus compounds such as triphenylphosphine. Additives that can be used in the side-chain chlorination of the 3-methylphenyl chloroformate are, for example, pyridine, pyridine derivatives such as methylpyridines or chloropyridines, amides such as acetamide or benzamide, biuret, urea, cyclic lactams, urethanes, amines or polyamines such as urotropin, ethanolamine, or tetraethylenepentamine, phosphorus compounds such as phosphorus trichloride or phosphorus pentachloride, or sulfur compounds such as diaryl sulfides and diaryl disulfides.

As chlorinating agent in the side-chain chlorination of 3-methylphenyl chloroformate, it is possible to use, for example, chlorine or sulfuryl chloride.

The process of the invention is advantageously carried out using 3-chloromethylphenyl chloroformate containing less than 1% by weight of 3-methylphenyl chloroformate that has not been chlorinated in the side chain and less than 5% by weight of more highly chlorinated 3-bischloromethylphenyl chloroformate.

The 3-chloromethylphenyl chloroformate is, according to the invention, acidolyzed using a carboxylic acid or a carboxylic acid salt. The product of this reaction is the diester of 3-hydroxybenzyl alcohol with the carboxylic acid used.

According to the invention, a broad range of aliphatic, cycloaliphatic, and aromatic carboxylic acids can be used as carboxylic acid. Suitable aliphatic carboxylic acids are, for example, carboxylic acids having linear or branched alkyl radicals having from 1 to 12 carbon atoms, preferably from 1 to 6 carbon atoms. Examples that may be mentioned are formic acid, acetic acid, propionic acid, butyric acid, and 2-methylpropionic acid.

Suitable cycloaliphatic carboxylic acids are, for example, those having from 4 to 11 carbon atoms, preferably from 4 to 7 carbon atoms. Examples that may be mentioned are cyclopropanecarboxylic acid, cyclopentanecarboxylic acid, and cyclohexanecarboxylic acid.

Aromatic carboxylic acids that can be used are, for example, those having from 7 to 12 carbon atoms, preferably from 7 to 10 carbon atoms. An example that may be mentioned is benzoic acid.

The aliphatic and cycloaliphatic carboxylic acids may optionally bear, for example, from one to three additional substituents, for example, halogen atoms such as fluorine, chlorine, and/or bromine, preferably fluorine and/or chlorine.

The aromatic carboxylic acids can likewise bear, for example, from one to three substituents, for example, halogen atoms such as fluorine, chlorine, and/or bromine and/or $C_1$–$C_6$-alkyl groups such as methyl, ethyl, n-propyl, i-propyl, n-butyl, t-butyl, hexyl, and/or cyclohexyl.

As carboxylic acid salts, it is possible to use, for example, salts of alkali metals and alkaline earth metals and ammonium salts. Preference is given to alkali metal salts such as sodium salts and ammonium salts. The acid part of the carboxylic acid salts can correspond to the above-described aliphatic, cycloaliphatic, and aromatic carboxylic acids.

The amount of carboxylic acid and/or carboxylic acid salt to be used depends on the way in which the reactants 3-chloromethylphenyl chloroformate and carboxylic acid and/or carboxylic acid salt are brought into contact.

If for example, only one carboxylic acid is brought into contact with 3-chloromethylphenyl chloroformate, only the chloroformate group reacts with the carboxylic acid and the chloromethyl group remains largely unaltered. The chloromethyl group can then also be reacted by subsequent addition of carboxylic acid salt. The stoichiometrically required amounts of carboxylic acid and carboxylic acid salt are in this case each time 1 mol per mol of 3-chloromethylphenyl chloroformate. When liquid carboxylic acids are used, these can advantageously also serve as solvents for the acidolysis reaction, and in this case preference is thus given to using from 1 to 20 mol of carboxylic acid (particularly from 1 to 10 mol of carboxylic acid) and from 1 to 5 mol of carboxylic acid salt (particularly from 1 to 2 mol of carboxylic acid salt), in each case per mol of 3-chloromethylphenyl chloroformate.

If, for example, the carboxylic acid salt is brought directly into contact with 3-chloromethylphenyl chloroformate in the presence or absence of a carboxylic acid, 1 mol of carboxylic acid salt is consumed by the acidolysis of the chloroformate group and 1 mol is consumed by acidolysis of the chloromethyl group, so that in this case 2 mol of carboxylic acid salt are stoichiometrically required for complete acidolysis. In this case, preference is given to using from 2 to 5 mol of carboxylic acid salt (particularly from 2 to 3 mol of carboxylic acid salt) per 1 mol of 3-chloromethylphenyl chloroformate.

The carboxylic acid salt can either be used as such or can be prepared in situ from a carboxylic acid and a base. Suitable bases are, for example, alkali metal hydroxides and alkaline earth metal hydroxides, alkali metal carbonates and alkaline earth metal carbonates, and ammonia. Examples of suitable bases are NaOH, KOH, LiOH, $Na_2CO_3$, $K_2CO_3$, $Mg(OH)_2$, $Ca(OH)_2$, and/or $NH_3$. Preference is given to adding carboxylic acid salt as such.

It is also possible to use mixtures of various carboxylic acids and various carboxylic acid salts. However, preference is given to using one carboxylic acid and one of its salts.

The reaction of 3-chloromethylphenyl chloroformate with the carboxylic acid and/or the carboxylic acid salt according to the invention can be carried out in the presence or one of an inert solvent. Examples of suitable solvents are aromatic and chloroaromatic hydrocarbons such as benzene, toluene, xylene, chlorobenzene, chlorotoluenes, dichlorobenzenes, and trichlorobenzenes, etherified aromatics such as anisole, substituted anisoles, and phenethole, aromatic nitriles such as benzonitrile, tolunitriles, and chlorobenzonitrile, hydrogenated aromatic hydrocarbons such as decalin, and/or aliphatic polyethers such as 1,2-dimethoxyethane.

The acidolysis is preferably carried out in an excess of liquid carboxylic acid as solvent.

The acidolysis according to the invention can, for example, be carried out at temperatures in the range from 20 to 200° C., preferably from 50 to 150° C.

The pressure during the acidolysis reaction can be superatmospheric, subatmospheric, or atmospheric. Preference is given to pressures in the range from 0.9 to 3 bar.

The diesters prepared in the first reaction step can be isolated from the reaction mixture by, for example, distillation or aqueous work-up. Any inorganic salts obtained here can be removed by washing with water and the diester can be isolated by phase separation.

According to the invention, diesters of 3-hydroxybenzyl alcohol are obtained as a result of the acidolysis carried out in the first step. These diesters generally contain, as a result of partial hydrolysis in the aqueous work-up and/or as a result of water present in the acidolysis reaction, a certain proportion of a monoester of 3-hydroxybenzyl alcohol, but this is converted into 3-hydroxybenzyl alcohol in the same way as the diester in the subsequent alcoholysis. The monoester content can be, for example, up to 50% by weight.

According to the invention, these diesters are converted into 3-hydroxybenzyl alcohol by reaction with an alcohol (i.e., alcoholysis).

Alcohols which can be used for this alcoholysis are, for example, aliphatic alcohols having from 1 to 12 carbon atoms or cycloaliphatic alcohols having from 5 to 12 carbon atoms. Preference is given to linear and branched aliphatic alcohols having from 1 to 6 carbon atoms and cycloaliphatic alcohols having from 5 to 8 carbon atoms. Examples that may be mentioned are methanol, ethanol, n-propanol, i-propanol, n-butanol, i-butanol, t-butanol, n-pentanol, n-hexanol, cyclohexanol, and methylcyclohexanols.

It is also possible to use aromatic alcohols having, for example, from 6 to 10 carbon atoms, e.g., phenol, cresols, xylenols, and naphthols, as alcohols.

The aliphatic, cycloaliphatic, and aromatic alcohols may be substituted, for example, by halogen atoms such as fluorine, chlorine, or bromine, preferably fluorine or chlorine. If substituted, the alcohols can bear one or more substituents.

The stoichiometrically required amount of alcohol to be used is 2 mol per mol of diester of 3-hydroxybenzyl alcohol. However, since equilibria between the diester, the two monodeacylated intermediates, 3-hydroxybenzyl alcohol, the alcohol added, and the respective carboxylic ester of the alcohol are generally established, it is advantageous to shift the equilibria towards 3-hydroxybenzyl alcohol, for example, by using an excess of alcohol or by removing (e.g., by distillation) the alcohol carboxylate formed, in order to achieve complete conversion into the desired 3-hydroxybenzyl alcohol. Since in the case of removal of alcohol carboxylate by distillation, azeotropes composed of the alcohol and its carboxylic ester are frequently present, it is advantageous in both cases to use the alcohol in excess, for example, in amounts of from 2.1 to 20 mol (preferably from 2.5 to 10 mol) per mol of diester of 3-hydroxybenzyl alcohol.

To accelerate the alcoholysis of the diester, catalysts can be added. Catalysts that can be used are, for example, those that are known for alcoholysis of carboxylic esters, for example, bases, acids, and metal salts or metal compounds. Examples of suitable bases are alkali metal hydroxides and alkaline earth metal hydroxides, alkali metal carbonates and alkaline earth metal carbonates, amines, and phosphines, particularly LiOH, NaOH, KOH, $Na_2CO_3$, $K_2CO_3$, $Mg(OH)_2$, and $Ca(OH)_2$. Examples of suitable acids are mineral acids, carboxylic acids, and sulfonic acids, particularly $H_2SO_4$, $H_3PO_4$, HCl, HBr, HI, acetic acid, propionic acid, and benzoic acid. Suitable metal salts and metal compounds are, for example, salts and compounds of thallium, tin, and titanium, e.g., $TlNO_3$, $(butyl)_2SnO$, and $Ti(O\text{-}phenyl)_4$.

The catalysts can also be present in immobilized form, for example, in the form of basic or acidic ion exchangers that, for example, bear amine or $HSO_3$ functions or the appropriate metal as cation.

Catalysts can, for example, be used in amounts of from 0.05 to 10 mol % (preferably from 0.5 to 3 mol %), based on the diester of 3-hydroxybenzyl alcohol. If relatively small amounts of catalyst within these ranges are used, the work-up of the reaction mixture from the alcoholysis is simplified.

In the case of immobilized catalysts, the term mol % refers to the active functional groups of the catalyst.

The alcoholysis of the invention is preferably carried out using acidic catalysts such as $H_2SO_4$, $H_3PO_4$, HCl, Hbr, or acidic ion exchangers.

The alcoholysis of the diester of 3-hydroxybenzyl alcohol can be carried out in the presence or absence of inert solvents. For example, it is possible to use the same solvents that have been mentioned above for the acidolysis of 3-chloromethylphenyl chloroformate by means of carboxylic acid and/or its salts. However, the acidolysis is preferably carried out without addition of solvents.

Mixtures of various alcohols can also be used as alcohols and mixtures of various catalysts can be used as catalysts.

The alcoholysis of the diester of 3-hydroxybenzyl alcohol can be carried out, for example, at temperatures in the range from 0 to 200° C., preferably from 50 to 150° C.

The pressure in the alcoholysis reaction can be superatmospheric, subatmospheric, or atmospheric. Preference is given to atmospheric pressure, subatmospheric pressures that may be necessary for distilling off a relatively high-boiling carboxylic ester, and superatmospheric pressures that may be necessary for overcoming an azeotrope. Accordingly, the reaction pressure is, for example, from 0.01 to 10 bar, preferably from 0.1 to 5 bar.

The process of the invention can be carried out in various embodiments. In principle, each of the two substeps can be carried out continuously, batchwise, or semicontinuously in portions.

In a preferred embodiment, the carboxylic acid (e.g., acetic acid) is placed in the reaction vessel and heated to reflux temperature, and 3-chloromethylphenyl chloroformate is then metered in while stirring, with essentially only the chloroformate group being acidolyzed. The carboxylic acid salt (e.g., sodium acetate) is then added to the fully reacted mixture and the mixture is stirred hot. This results in acidolysis of the chloromethyl group. In this way, the acetic diester of 3-hydroxybenzyl alcohol is obtained after, for example, aqueous work-up.

In the aqueous work-up, for example, the carboxylic acid present as solvent is distilled from the reaction mixture and the residue obtained is stirred with water to remove the salts.

As a result of hydrolysis during this work-up, and also as a result of hydrolysis by water that may be present in the acidolysis reaction, part of the diester can be deacylated to form a monoester of hydroxybenzyl alcohol. This monoacylation product of 3-hydroxybenzyl alcohol is obtained in admixture with the diester. It is one of the intermediates in the subsequent alcoholysis of the diester to form 3-hydroxybenzyl alcohol, so that it is likewise converted into the desired product 3-hydroxybenzyl alcohol.

Catalyst and an excess of alcohol (e.g., methanol or ethanol) are then added to the diester that has been prepared and the carboxylic ester (e.g., methyl or ethyl acetate) formed is distilled off as an azeotrope with the alcohol. If desired, further alcohol can be introduced into the reaction mixture continuously or semicontinuously in portions during the distillation to achieve complete conversion. After the reaction, the alcohol is then evaporated together with remaining carboxylic ester. The residue that remains an, if necessary, be purified by recrystallization. In another preferred embodiment, a mixture of carboxylic acid (e.g., acetic acid) and its salt (e.g., sodium acetate) is placed in a reaction vessel and 3-chloromethylphenyl chloroformate is metered in hot. After complete reaction and aqueous work-up, the acetic diester of 3-hydroxybenzyl alcohol is also obtained in this way and can then be alcoholyzed as described above.

Due to the change to a completely novel starting material for this purpose, the process of the invention has a series of advantages. First, readily available and inexpensive 3-chloromethylphenyl chloroformate is used as starting material. Second, the process requires simple auxiliaries such as carboxylic acids, carboxylic acid salts, and alcohols that are available at low cost and require no particular measures in their handling. For this reason, the process of the invention enables 3-hydroxybenzyl alcohol to be obtained in a significantly simpler and cheaper way than hitherto.

The following example further illustrates details for the process of this invention. The invention, which is set forth in the foregoing disclosure, is not to be limited either in spirit or scope by this example. Those skilled in the art will readily understand that known variations of the conditions of the following procedure can be used. Unless otherwise noted, all temperatures are degrees Celsius and all percentages are percentages by weight.

EXAMPLE 100 parts by weight of acetic acid were placed in a reaction vessel and stirred at 120° C. 60.3 parts by weight of 3-chloromethylphenyl chloroformate (assay according to GC area: 98.0%) were then metered in over a period of 1 hour. The mixture was then stirred for another 1 hour at 120–125° C., after which it was cooled to 80° C. 31.9 parts by weight of sodium acetate were then added while stirring and the mixture was stirred under reflux for another 7 hours. After the major part of the acetic acid still present had been distilled off, first at atmospheric pressure and finally under reduced pressure down to 22 mbar, the residue was taken up in 100 parts by weight of water, and the organic phase was separated off and washed once more with 22 parts by weight of water. The aqueous phases were discarded. This gave 58.2 parts by weight of an oily product that, according to GC analysis, contained 78.3% of the acetic diester of 3-hydroxybenzyl alcohol and 19.2% of a monoacetylated derivative of 3-hydroxybenzyl alcohol.

This mixture was admixed with 55.4 parts by weight of methanol and 0.58 parts by weight of concentrated sulfuric acid and refluxed in a column (10 theoretical plates). Over a period of 4 hours, 75 parts by eight of methanol/methyl acetate azeotrope were taken off and the same amount of methanol was added to the reaction mixture in the bottom of the column. This gave 104.8 parts by weight of a methanolic solution of 3-hydroxybenzyl alcohol containing 32.2% of 3-hydroxybenzyl alcohol (HPLC). The yield was thus 94.4% of theory based on the amount of 3-chloromethylphenyl chloroformate used.

The 3-hydroxybenzyl alcohol thereby prepared could be isolated in pure form by evaporation of the methanol and recrystallization, for example, from benzene or carbon tetrachloride.

What is claimed is:

1. A process for preparing 3-hydroxybenzyl alcohol comprising
   (a) subjecting 3-chloromethylphenyl chloroformate to an acidolysis with a carboxylic acid or a carboxylic acid salt, and
   (b) carrying out an alcoholysis of the reaction product of the acidolysis step.

2. A process according to claim 1 wherein the 3-chloromethylphenyl chloroformate contains less than 1% by weight of 3-methylphenyl chloroformate that has not been chlorinated in the side chain and less than 5% by weight of more highly chlorinated 3-bischloromethylphenyl chloroformate.

3. A process according to claim 1 wherein the acidolysis is carried out using (i) a carboxylic acid containing linear or branched alkyl radicals having from 1 to 12 carbon atoms or (ii) a cycloaliphatic carboxylic acid containing from 4 to 11 carbon atoms or (ii) an aromatic carboxylic acid containing from 7 to 12 carbon atoms.

4. A process according to claim 1 wherein 1 to 20 mol of a carboxylic acid is brought into contact with 3-chloromethylphenyl chloroformate and 1 to 5 mol of a carboxylic acid salt is subsequently added.

5. A process according to claim 1 wherein 2 to 5 mol of a carboxylic acid salt is brought directly into contact with 3-chloromethylphenyl chloroformate.

6. A process according to claim 1 wherein the acidolysis is carried out at temperatures in the range from 20 to 200° C. and pressures in the range from 0.9 to 3 bar.

7. A process according to claim 1 wherein the alcoholysis is carried out using an aliphatic alcohol having from 1 to 18 carbon atoms, a cycloaliphatic alcohol having from 5 to 12 carbon atoms, or an aromatic alcohol having from 6 to 11 carbon atoms.

8. A process according to claim 1 wherein the alcoholysis is carried out using from 2.1 to 20 mol of an alcohol per 1 mol of the diester of 3-hydroxybenzyl alcohol formed in the first step.

9. A process according to claim 1 wherein the alcoholysis is carried out in the presence of a catalyst.

10. A process according to claim 1 wherein the alcoholysis is carried out at temperatures in the range from 0 to 200° C. and at pressures in the range from 0.01 to 10 bar.

* * * * *